United States Patent [19]

Carbonneil

[11] Patent Number: Plant 5,839

[45] Date of Patent: Dec. 23, 1986

[54] PEACH TREE (PRIMECREST)

[75] Inventor: Georges Carbonneil, Vinca, France

[73] Assignee: S.A.R.L. Castang, Gardonne, France

[21] Appl. No.: 686,132

[22] Filed: Dec. 24, 1984

[51] Int. Cl.[4] ..... A01H 5/03

[52] U.S. Cl. ..... Plt./43

[58] Field of Search ..... Plt./43

*Primary Examiner*—R. E. Bagwill

*Attorney, Agent, or Firm*—Roger B. Webster

[57] ABSTRACT

A peach tree which is of medium size and vigor, spreading, open, vase form, and half-hardy; foliated with large, lanceolate, acuminate leaves having a serrate margin, long, medium-thick petiole, and alternate, medium to small, globose, yellowish-green glands positioned on the petiole; blooms early from hardy, large, medium size, plump, appressed-to-free flower buds; the flowers being medium size, showy, and white to slightly pink in color; and is a regular and very productive bearer of uniform, medium size, symmetrical, globose, semi-freestone fruit having bright orange-yellow skin substantially overspread with red, and yellow flesh.

1 Drawing Figure

BACKGROUND OF THE VARIETY

Field of the Invention

As the owner of farmland, including an orchard of peach trees, located at Sainte Madeline, Pyrenees-Orientales, France, I frequent such land for the purpose of the care and maintenance thereof and the orchard thereon, and against this background of my activities as a fruit grower, the present variety of peach tree was discovered by me.

CLASSIFICATION OF THE VARIETY

The present variety of peach tree is embraced by Class 43, Plants, of the U.S. Patent Office Manual Of Classification.

PRIOR VARIETIES

Among existing varieties of peach trees which are known to me and mentioned herein, is the Springcrest (unpatented).

ORIGIN OF THE VARIETY

The present variety of peach tree was discovered by me growing as a full-scaffold limb on a Springcrest peach tree in my orchard located as aforesaid; it having been observed by me that such full-scaffold limb bore fruit having an earlier ripening period than the remainder of the fruit on the host tree. Such full-scaffold limb was—after my discovery of it—maintained under close and continuing observation in order to confirm such earlier ripening period of its fruit, and other characteristics which I recognized.

ASEXUAL REPRODUCTION OF THE VARIETY

The present variety of peach tree was asexually reproduced by me by budding on compatible seedlings, and—in maturity—such reproductions remained stable and ran true in all respects to the original varietal discovery.

SUMMARY OF THE VARIETY

The present variety of peach tree is, characteristically, of medium size and vigor, spreading, open, vase form, and half-hardy; foliated with large, lanceolate, acuminate leaves having a serrate margin, long, medium-thick petiole, and alternate, medium to small, globose, yellowish-green glands positioned on the petiole; blooms early from hardy, large, medium size, plump, appressed-to-free flower buds; the flowers being medium size, showy, and white to slightly pink in color; and is a regular and very productive bearer of uniform, medium size, symmetrical, globose, semi-freestone fruit having bright orange-yellow skin substantially overspread with red, and yellow flesh.

The present variety of peach tree is further, and more particularly, characterized by leaves slightly dimensionally variable from Springcrest and fruit which—while similar to the fruit of Springcrest in form, color, and size—has a distinctive, narrow yellow ventral suture line, and the ripening date of the fruit is approximately two and one-half weeks earlier than the Springcrest.

Additionally, in comparison to the Springcrest, the tree of the present variety is slightly more spreading, and the leaves (including the blade and petiole) are slightly longer but of slightly less blade width.

BRIEF DESCRIPTION OF THE DRAWING

The drawing is an illustration, by photographic reproduction in color, of a twig with leaves, and fruit of the variety; one fruit being cut into halves with the stone remaining in place in one half.

DESCRIPTION OF THE VARIETY

The botanical details of this new and distinct variety of peach tree—with color definitions in common color terms—are as follows:

Tree:

*Size.*—Medium.
*Vigor.*—Medium.
*Growth.*—Spreading.
*Density.*—Open.
*Form.*—Vase-formed.
*Hardiness.*—Half hardy.
*Production.*—Very productive.
*Bearing.*—Regular bearer.

Trunk:

*Size.*—Medium.
*Texture.*—Medium.

Branches:

*Size.*—Medium.
*Texture.*—Medium.
*Color.*—Brown.
*Lenticels.*—Number: Medium.
*Size.*—Medium.

Leaves:
*Size.*—Large. Average length—18.45 cm. Average width—4.24 cm.
*Form.*—Lanceolate. Acuminate.
*Thickness.*—Thick.
*Color.*—Dark green.
*Texture.*—Smooth.
*Margin.*—Serrate.
*Petiole.*—Long (average length—1.38 cm.). Medium thickness.
*Glands.*—Average number—3.7. Alternate. Medium to small. Globose. Yellowish green. Positioned on petiole.
*Stipules.*—Wanting.

Flower buds:
*Hardiness.*—Hardy.
*Size.*—Large.
*Length.*—Medium.
*Form.*—Plump. Appressed to free.

Flowers:
*Blooming period.*—Date of first bloom: Mar. 15, 1983. Date of full bloom: Mar. 20, 1983. Early — about with Springcrest.
*Size.*—Medium.
*Appearance.*—Showy.
*Color.*—White to slightly pink.

Fruit:
*Maturity when described.*—Hard ripe — June 4, 1983.
*Date of first picking.*—May 30, 1983.
*Date of last picking.*—June 6, 1983.
*Size.*—Uniform. Medium. Average diameter axially — 6.4 cm. Average transversely in suture plane — 5.7 cm.
*Form.*—Uniform. Symmetrical. Globose.
*Suture.*—Distinct. Shallow. Extends from base to apex, with slight depression beyond pistil point. Narrow yellow ventral suture line.
*Ventral surface.*—Rounded slightly. Lipped toward base and apex.
*Lips.*—Equal.
*Cavity.*—Flaring. Circular. Depth range — 0.8 cm. to 1.0 cm. Breadth range — 2.5 cm. to 3.0 cm.
*Base.*—Rounded.
*Apex.*—Short Depressed.
*Pistil point.*—Apical.

Skin:
*Thickness.*—Medium.
*Tenacity.*—Free.
*Tendency to crack.*—None.
*Color.*—Bright orange-yellow substantially overspread with red. (60% dark red to 20% lighter red washed over 20% bright orange-yellow).

Flesh:
*Color.*—Yellow. Surface of pit cavity Yellow.
*Amygdalin.*—Moderate.
*Juice.*—Abundant.
*Texture.*—Medium. Fine. Melting.
*Fibers.*—Few. Tender.
*Ripens.*—Earliest at apex.
*Flavor.*—Subacid to mild.
*Aroma.*—Distinct.
*Eating quality.*—Good.

Stone:
*Type.*—Semi-free. Adheres to flesh along both dorsal and ventral edges.
*Fibers.*—Short. Retains short fiber-like threads along ridges.
*Size.*—Small. Average length — 2.9 cm. Average breadth — 2.2 cm. Average thickness — 1.7 cm.
*Form.*—Oval.
*Base.*—Straight.
*Apex.*—Acute.
*Sides.*—Equal.
*Surface.*—Irregularly furrowed near base.
*Ridges.*—Rounded on either side. Continuous.
*Pits.*—Circular to elongated.
*Ventral edge.*—Thick, with wing toward base.
*Dorsal edge.*—Full, with deep groove.
*Color.*—Whitish beige.
*Tendency to split.*—Slight.

Use: Market. Dessert.
Keeping quality: Medium.
Shipping quality: Good.
Resistance to insects and diseases: Medium. Testing on susceptible virus disease indicators evidences freedom from known virus diseases.

The peach tree and its fruit herein described may vary in slight detail due to climatic and soil conditions under which the variety may be grown; the present description being of the variety as grown in southern France.

I claim:

1. A new and distinct variety of peach tree, substantially as illustrated and described, characterized in particular by the regular and very productive bearing of semi-freestone fruit which—while similar to the Springcrest in form, color, and size—ripens approximately two and one-half weeks earlier than the Springcrest.

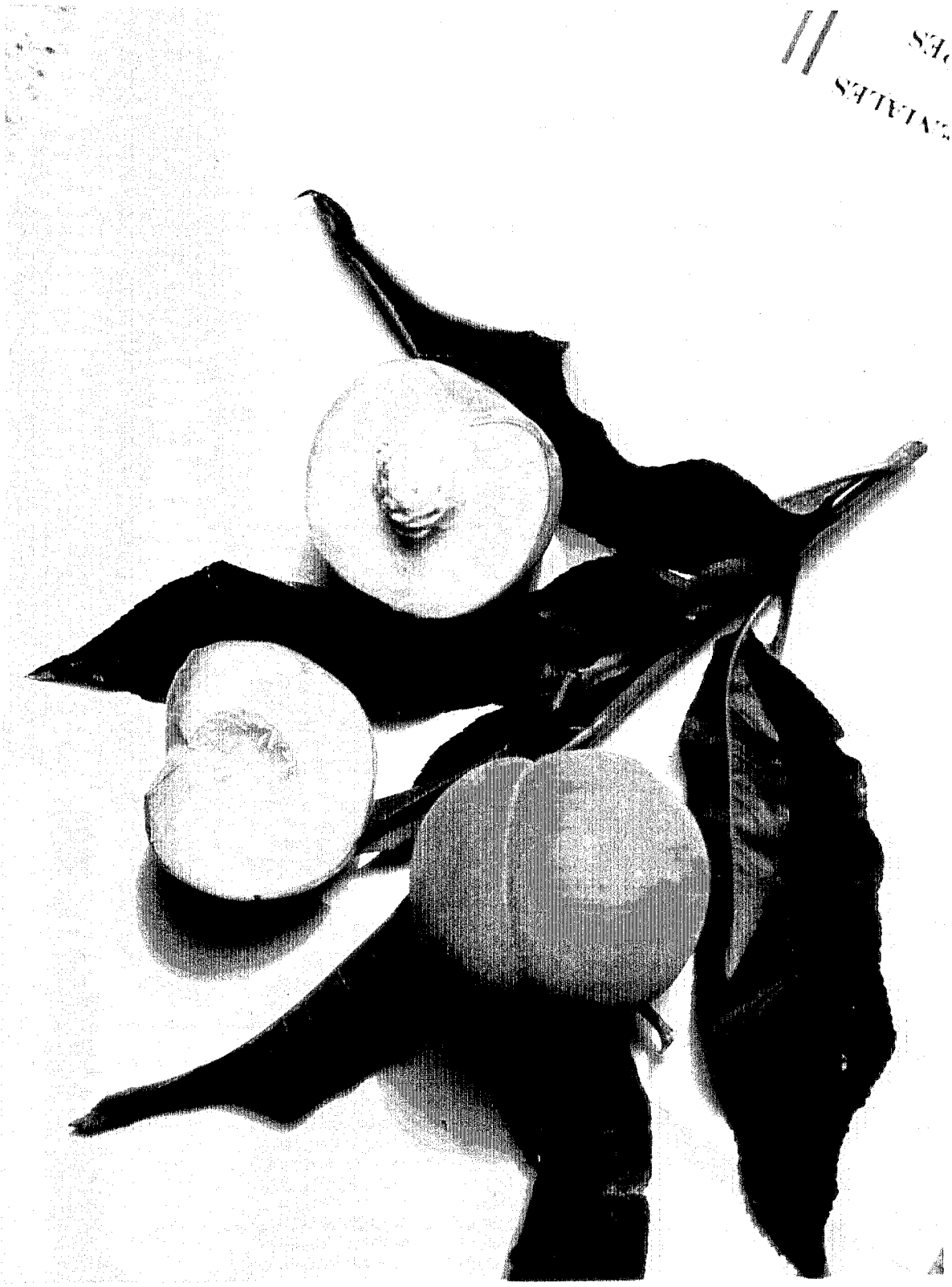

* * * * *